United States Patent [19]

Georges

[11] Patent Number: 4,647,700
[45] Date of Patent: Mar. 3, 1987

[54] PROCESS FOR THE PREPARATION OF META-CHLOROANILINES

[75] Inventor: Cordier Georges, Francheville, France

[73] Assignee: Rhone-Poulenc Agrochimie, Lyons, France

[21] Appl. No.: 780,212

[22] Filed: Sep. 26, 1985

Related U.S. Application Data

[63] Continuation of Ser. No. 518,968, Aug. 1, 1983, abandoned.

[30] Foreign Application Priority Data

Aug. 24, 1982 [FR] France ................................ 82 14682

[51] Int. Cl.$^4$ ............................................. C07C 85/24
[52] U.S. Cl. ..................................................... 564/412
[58] Field of Search ........................................... 564/412

[56] References Cited

U.S. PATENT DOCUMENTS

| | | |
|---|---|---|
| 4,085,141 | 4/1978 | Wedemeyer et al. ............... 564/412 |
| 4,206,147 | 6/1980 | Daumas et al. ...................... 564/412 |
| 4,206,148 | 6/1980 | Biola et al. .......................... 564/412 |
| 4,329,914 | 4/1982 | Cordier ................................ 564/412 |
| 4,340,759 | 7/1982 | Cordier ................................ 564/412 |
| 4,351,959 | 9/1982 | Cordier ................................ 564/412 |
| 4,418,213 | 11/1983 | Cordier et al. ...................... 564/412 |
| 4,429,156 | 1/1984 | Wedemeyer et al. ............... 564/412 |

*Primary Examiner*—Paul F. Shaver
*Attorney, Agent, or Firm*—Burns, Doane, Swecker & Mathis

[57] ABSTRACT

This invention relates to a process for the preparation of meta-chloroanilines. Polychloroanilines containing at least one chloroatom in the meta position are reacted with hydrogen iodide in a homogeneous aqueous or organic medium at a temperature between about 90° and 250° C. Gaseous hydrogen and solid catalysts are not required. The meta-chloroanilines are useful in the manufacture of agrochemical intermediates.

15 Claims, No Drawings

PROCESS FOR THE PREPARATION OF META-CHLOROANILINES

This application is a continuation of application Ser. No. 518,968, filed 08/01/83, now abandoned.

The present invention relates to a process for the preparation of anilines substituted by chlorine in the meta position, by the dechlorination of more highly chlorinated aromatic amines. These meta-chloroanilines are intermediates, in particular for the manufacture of agrochemical active ingredients.

Numerous processes have already been proposed for the preparation of anilines chlorinated in the meta position, by the hydrodechlorination of polychloroanilines with hydrogen under pressure, in a liquid medium, in the presence of a strong acid and a catalyst based on a noble metal. These processes require high pressures, which, in association with relatively high temperatures and acidic conditions, make it necessary to carry out the reactions in an autoclave, giving rise to serious corrosion problems. Attempts have been made to moderate the temperature and pressure by carrying out the reactions in the presence of iodine-based derivatives, but heterogeneous metal catalysts always have to be used.

The object of the present invention is to prepare meta-substituted chloroanilines by the selective removal of chlorine atoms by an even simpler method which is therefore easier to carry out industrially.

The invention relates more particularly to a process for the preparation of anilines substituted in the meta position by chlorine, of the general formula:

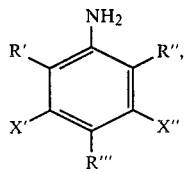
B in which:
X' and X'', which are identical or different, each represent a chlorine atom, an alkyl radical containing from 1 to 4 carbon atoms or an alkoxy radical containing from 1 to 4 carbon atoms, at least one of the symbols X' and X'' necessarily being a chlorine atom and it also being possible for one of the symbols X' and X'' to be a hydrogen atom, and R', R'' and R''', which are identical or different, each represent a chlorine atom, an alkyl radical containing from 1 to 4 carbon atoms, an alkoxy radical containing from 1 to 4 carbon atoms or a phenyl, benzyl or phenoxy radical, it being possible for the phenyl nucleus of these radicals to be substituted by at least one halogen atom, in particular a chlorine atom, an alkyl radical containing from 1 to 4 carbon atoms or an alkoxy radical having 1 to 4 carbon atoms, it being possible for at most two of them to be a hydrogen atom, by reacting a polychloroaniline of the general formula:

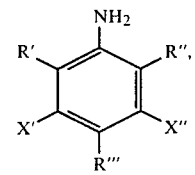
A in which X', X'', R', R'' and R''' have the same meanings as above, with the additional proviso that at least one of the symbols R', R'' and R''' represents a chlorine atom, with hydrogen iodide, in the liquid phase, according to the equation:

$$A + 2nHI \rightarrow B + nI_2 + nHCl,$$

in which n is an integer from 1 to 3, representing the number of chlorine atoms to be removed per mol of the polychloroaniline A.

The amount of hydrogen iodide which must be used in the reaction is at least the stoichiometric amount and preferably an excess, i.e. the molar ratio (HI/n) is generally between 2/1 and 20/1 and preferably between 2/1 and 10/1.

The reaction is carried out either in an aqueous medium, in which case the hydrogen iodide is used in the form of a solution of hydriodic acid, or in an organic medium in an organic solvent which is inert under the reaction conditions and, in particular, towards the hydrogen iodide used and the iodine produced and also towards the hydrogen chloride, such as e.g. an aromatic solvent like toluene or xylene, a chlorinated aromatic solvent like a chlorobenzene, or a chlorinated aliphatic solvent.

To accelerate the reaction, a strong acid can advantageously be added to the reaction medium; it is either a mineral acid such as hydrochloric acid or sulphuric acid, when the reaction is carried out in an aqueous medium, or an organic acid such as acetic acid, trichloroacetic acid, trifluoroacetic acid, methanesulphonic acid or para-toluenesulphonic acid, when the reaction is carried out in an organic solvent medium.

Of course, the hydrogen iodide can either be used as such or be formed in situ under the reaction conditions, e.g. from a mixture of an alkali metal iodide and hydrochloric acid.

Furthermore, in an organic medium, as the reaction releases hydrogen chloride, the pressure of the latter increases: there is no disadvantage in carrying out the reaction under autogenous pressure, but it is preferred industrially to limit the pressure to at most 100 bars and preferably to at most 50 bars. To do this, the reaction is carried out under a stream of HI with continuous removal of the HCl formed.

The reaction temperature is generally between 90° and 250° C. and preferably from 110° to 220° C. At lower temperatures, the reaction is slow and, furthermore, the amine hydroiodides are not completely soluble in the medium. Above 100° C., the medium is homogeneous and the reaction takes place with a virtually quantitative yield, the temperature increase having the effect of accelerating the reaction. Furthermore, it is no longer industrially advantageous to carry out the reaction above 250° C.

As compounds of the formula A which can be used to carry out the process, there may be mentioned, in particular, those in whose formulae R', R'' and R''' represent a hydrogen or chlorine atom, i.e. 2,3,4,5-, 2,3,4,6- and 2,3,5,6-tetrachloroanilines and also pentachloroaniline, preference being given to 3,4- and 2,3-dichloroanilines, 3,4,5-trichloroaniline and 2,3,4,5- and 2,3,5,6-tetrachloroanilines.

Amongst the meta-chloroanilines of the formula B which can be prepared by the process according to the invention, there may be mentioned, in particular, those in whose formulae R', R" and R''' represent a hydrogen or chlorine atom, i.e. 2,3-, 2,5- and 3,4-dichloroanilines, 2,3,4-, 2,3,5-, 2,3,6-, 2,4,5- and 3,4,5-trichloroanilines and, preferably, 3-chloroaniline and 3,5-dichloroaniline. These chloroanilines can be obtained either by themselves or in mixtures, depending on the starting composition and the degree of conversion.

The process according to the invention can be carried out continuously or batchwise. At the end of the reaction, the meta-chloroaniline obtained can be separated off by any means which is in itself known, e.g. by solvent extraction and/or by distillation.

The process according to the invention makes it possible selectively to obtain meta-chloroanilines under conditions which are particularly advantageous for its industrial use, since the reaction is carried out in a completely homogeneous medium, without a catalyst and at very moderate pressures.

The examples which follow are given by way of indication, but without implying a limitation, in order to illustrate the invention. The degrees of conversion and the yields are molar ratios.

EXAMPLE 1

2,3,4,5-Tetrachloroaniline (0.1 mol) and an aqueous solution containing 8 mol/liter of hydriodic acid (50 ml) are introduced into a pressure-resistant tantalum-lined reactor of 200 cc capacity.

The mixture is heated for 16 hours at 135° C. under autogeneous pressure, with stirring.

After this reaction time, water and toluene (or monochlorobenzene) are added to the cooled reaction medium in sufficient amounts to give two clear liquid phases. These are separated by decantation and the iodine is removed from the aqueous phase by a series of extractions with toluene (or with monochlorobenzene). The organic phase is distilled under atmospheric pressure, which makes it possible to separate off virtually all the iodine from the polychloroanilines.

The organic residue is analysed by vapour phase chromatography.

Under these conditions, it is observed that the degree of conversion (DC) of the 2,3,4,5-tetrachloroaniline is 99.5% and the actual yield of 3,5-dichloroaniline is 61.1%; 37.5% of 2,3,5-trichloroaniline, formed as an intermediate, remains.

If this reaction is repeated with a heating time of 32 hours, the actual yield of 3,5-dichloroaniline is quantitative.

EXAMPLES 2 TO 7

The procedure of Example 1 is followed with modification of the concentration of tetrachloroaniline (2,3,4,5-TTCA), the concentration of hydriodic acid (HI), the temperature (T) and the duration, hydrochloric acid (HCL) being added as the strong acid in two cases.

The table which follows gives the values of the parameters which vary, together with the degree of conversion of the 2,3,4,5-tetrachloroaniline and the actual yield of 3,5-dichloroaniline (3,5-DCA) and its intermediate 2,3,5-trichloroaniline (2,3,5-TCA). It should be noted that n is equal to 2 in this reaction.

If these experiments are repeated with twice the heating time, the actual yield of 3,5-dichloroaniline obtained is quantitative.

EXAMPLE 8

The procedure of Example 1 is followed, the 2,3,4,5-tetrachloroaniline being replaced by 2,3,5,6-tetrachloroaniline (0.05 mol) and the mixture being heated for 5 hours. It is found that, under these conditions, the degree of conversion of the 2,3,5,6-tetrachloroaniline is 96%, the actual yield of 3,5-dichloroaniline is 81.2%, and 14.7% of unconverted intermediate 2,3,5-trichloroaniline remains.

By following the above procedure but doubling the heating time, the degree of conversion of the tetrachloroaniline is 100% and the actual yield of 3,5-dichloroaniline is quantitative.

EXAMPLES 9 TO 15

The procedure of Examples 2 to 7 is followed, the 2,3,4,5-tetrachloroaniline being replaced by 3,4,5-trichloroaniline, n being equal to 1 in this case.

The table which follows gives the values of the parameters which vary, together with the actual yield of 3,5-dichloroaniline.

By following the above procedure but doubling the heating time, the actual yields of 3,5-dichloroaniline are quantitative.

EXAMPLES 16 AND 17

The procedure of Example 1 is followed, the 2,3,4,5-tetrachloroaniline being replaced successively by 3,4-dichloroaniline and 2,3-dichloroaniline, n being equal to 1 in these cases, each at a concentration of 2 mol/liter, the hydriodic acid being at a concentration of 8 mol/liter, the temperature being 135° C. and the duration being 5 hours.

Under these conditions, it is found that: 1/ the 3,4-dichloroaniline is converted to a degree of 48.4% and the yield of 3-chloroaniline is 91.5% relative to the 3,4-dichloroaniline converted; and 2/ the 2,3-dichloroaniline is converted to a degree of 37.5% and the yield of 3-chloroaniline is 88.2% relative to the 2,3-dichloroaniline converted.

EXAMPLES 18 AND 19

2,3,5,6-Tetrachloroaniline ($4 \times 10^{-3}$ mol), liquid hydrogen iodide ($16 \times 10^{-3}$ mol) and 1,2,4-trichlorobenzene (20 ml) are introduced into a pressure-resistant tantalum-lined reactor of 200 cc capacity.

The mixture is heated under autogenous pressure for 2 hours at 170° and 210° C. respectively.

After this reaction time, it is found that: a/ at 170° C., the degree of conversion of the 2,3,5,6-tetrachloroaniline is 63.4%, the actual yield of 3,5-dichloroaniline is 57.2%, and 6.2% of unconverted intermediate 2,3,5-trichloroaniline remains; and b/ at 210° C., the degree of conversion of the 2,3,5,6-tetrachloroaniline is 84.1%, the actual yield of 3,5-dichloroaniline is 80.6%, and 3.5% of unconverted intermediate 2,3,5-trichloroaniline remains.

If these two experiments are repeated with double the heating time, the actual yield of 3,5-dichloroaniline obtained is quantitative.

EXAMPLE 20

2,3,4,5-Tetrachloroaniline (0.06 mol) and 2,3,5,6-tetrachloroaniline (0.06 mol) are introduced, together with 1,2,4-trichlorobenzene (100 ml), into a 250 cc glass round-bottomed flask. The mixture is stirred and heated to 160° C. When this temperature is reached, a stream of dry gaseous hydrogen iodide. is passed through at a rate of 18 to 20 g/hour, with stirring, the temperature being kept at 160° C.

The gaseous effluent is collected in a bubbler containing water.

The reaction is stopped after 4 hours 20 minutes by shutting off the stream of gaseous hydrogen iodide. 80.5 g of the latter have been used.

The mixture is then subjected to distillation under atmospheric pressure 1,2,4-trichlorobenzene (150 ml) being added progressively. It is thus possible to separate virtually all the iodine from the polychloroanilines produced by the reaction.

The contents of the reactor are then cooled and neutralised with a dilute aqueous solution of sodium hydroxide, and the organic phase is analysed by gas chromatography. It is found that the degree of conversion of the tetrachloroanilines is 99.5% and that the yield of 3,5-dichloroaniline is 98.1%. 0.9% of trichloroanilines, formed as intermediates in the conversion, remains.

EXAMPLE 21

1,2-Dichlorobenzene (100 ml), 2,3-dichloroaniline (0.168 mol) and 3,4-dichloroaniline (0.072 mol) are introduced into a 250 cc three-necked round-bottomed flask. The mixture is heated to 160° C. and gaseous hydrogen iodide (0.66 mol; i.e. 2.75 mol of HI per mol of DCA) is passed in over a period of 4 hours, the reaction mixture being stirred.

After this time, the reaction mixture is cooled and treated in a conventional manner (as described in the previous examples), and analysis by vapour phase chromatography shows that the degree of conversion of the dichloroanilines is 96.5% and the yield of 3-chloroaniline is 100% relative to the dichloroanilines converted.

The iodine formed is recovered quantitatively. The excess hydrogen iodide is also recovered in the form of iodine, after oxidation with hydrogen peroxide in an acid medium.

TABLE I

| Example No. | [2,3,4,5-TICA] mol/liter | [HI] mol/liter | [HI]/n | [HCl] mol/liter | T °C. | Duration hours | DC % of TICA | AY % of 3,5-DCA | ADY % of 2,3,5-TCA |
|---|---|---|---|---|---|---|---|---|---|
| 2 | 2 | 8 | 2 | — | 135 | 16 | 99.5 | 61.1 | 37.5 |
| 3 | 1 | 4 | 2 | — | 135 | 5 | 97.6 | 19.1 | 78.5 |
| 4 | 1 | 8 | 4 | — | 135 | 5 | 10.0 | 91.6 | 7.4 |
| 5 | 1 | 4 | 2 | 6 | 135 | 5 | 99.5 | 56.5 | 43.4 |
| 6 | 2 | 8 | 2 | — | 163 | 1 | 98.0 | 57.2 | 36.5 |
| 7 | 0.5 | 2.4 | 2.4 | 7.6 | 163 | 1 | 100.0 | 81.8 | 13.6 |

TABLE II

| Example No. | [3,4,5-TICA] mol/liter | [HI] mol/liter | [HI]/n | [HCl] mol/liter | T °C. | Duration hours | DC % of B | AY % of 3,4,5-TCA |
|---|---|---|---|---|---|---|---|---|
| 1 | 2 | 4 | 2 | — | 135 | 16 | 70.5 | 70.5 |
| 10 | 2 | 6 | 3 | — | 135 | 5 | 90.3 | 90.3 |
| 11 | 2 | 8 | 4 | — | 135 | 5 | 98.0 | 98.0 |
| 12 | 2 | 8 | 4 | — | 135 | 2 | 93.5 | 93.5 |
| 13 | 2 | 4 | 2 | — | 163 | 1 | 69.5 | 69.5 |
| 14 | 2 | 4 | 2 | 4 | 163 | 1 | 78.0 | 78.0 |
| 15 | 2 | 8 | 4 | — | 105 | 16 | 86.0 | 86.0 |

I claim:

1. A process for forming a meta-chloroaniline B of the formula:

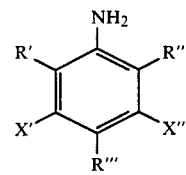

B wherein:
X' and X" are each independently a hydrogen atom, a chlorine atom, an alkyl group containing from 1 to 4 carbon atoms or an alkoxy group containing from 1 to 4 carbon atoms, except that at least one of X' and X" is a chlorine atom; and R', R" and R'" are each independently a hydrogen atom; a chlorine atom; an alkyl group containing 1 to 4 carbon atoms; an alkoxy group containing 1 to 4 carbon atoms; or phenyl, benzyl or phenoxy group, wherein the phenyl portion of said phenyl, benzyl or phenoxy is substituted by hydrogen or one or more halogen atoms, an alkyl group containing from 1 to 4 carbon atoms or an alkoxy group containing from 1 to 4 carbon atoms; except that at most two of R', R" and R'" are hydrogen atoms; which process comprises:

(1) forming a homogeneous liquid reaction mixture consisting essentially of:
(a) a polychloroaniline A of the formula:

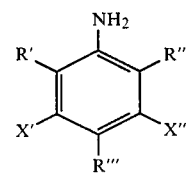

A wherein:

X', X", R' and R" are defined hereinabove, except that at least one of R', R" and R'" is a chlorine atom;
  (b) hydrogen iodide in an amount sufficient to react with A according to the equation:

$$A + 2nHI \rightarrow B + nI_2 + nHCl,$$

wherein n is an integer from 1 to 3, which represents the number of chlorine atoms to be removed per mole of polychloroaniline A; and
  (c) a solvent; and
(2) maintaining said reaction mixture between about 90° to 250° C. thereby forming a reaction product containing said meta-chloroaniline B.

2. The process according to claim 1, wherein the molar ratio of the hydrogen iodide to the number of chlorine atoms to be removed per mol of the starting polychloroaniline A is between 2/1 and 20/1.

3. The process according to claim 1, wherein the molar ratio of the hydrogen iodide to the number of chlorine atoms to be removed per mol of the starting polychloroaniline A is between 2/1 and 10/1.

4. The process according to claim 1, wherein said solvent is an aqueous medium.

5. The process according to claim 1, wherein said solvent is an inert organic solvent.

6. The process according to claim 5, wherein the organic solvent is a chlorobenzene.

7. A process for forming a meta-chloroaniline B of the formula:

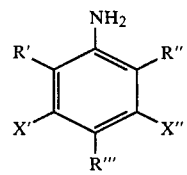

wherein:
X' and X" are each independently a hydrogen atom, a chlorine atom, an alkyl group containing from 1 to 4 carbon atoms or an alkoxy group containing from 1 to 4 carbon atoms, except that at least one of X' and X" is a chlorine atom; and
R', R" and R'" are each independently a hydrogen atom; a chlorine atom; an alkyl group containing 1 to 4 carbon atoms; an alkoxy group containing 1 to 4 carbon atoms; a phenyl, benzyl or phenoxy group, wherein the phenyl portion of said phenyl, benzyl or phenoxy is substituted by hydrogen or one or more halogen atoms, an alkyl group containing from 1 to 4 carbon atoms or an alkoxy group containing from 1 to 4 carbon atoms; except that at most two of R', R" and R'" are hydrogen atoms; which process comprises:
(1) forming a homogeneous liquid reaction mixture consisting essentially of:
  (a) a polychloroaniline A of the formula:

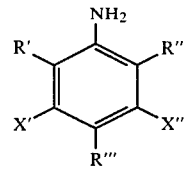

wherein:
X', X", R' and R" are defined hereinabove, except that at least one of R', R" and R'" is a chlorine atom;
  (b) hydrogen iodide in an amount sufficient to react with A according to the equation:

$$A + 2nHI \rightarrow B + nI_2 + nHCl,$$

wherein n is an integer from 1 to 3, which represents the number of chlorine atoms to be removed per mole of polychloroaniline A;
  (c) a solvent; and
  (d) in the presence of a strong acid; and
(2) maintaining said reaction mixture between about 90° to 250° C. thereby forming a reaction product containing said meta-chloroaniline B.

8. The process according to claim 7, wherein the strong acid (d) is hydrochloric acid.

9. The process according to claim 1, wherein in Step (2) said reaction mixture is maintained at a temperature between about 110° and 220° C.

10. The process according to claim 1, wherein the autogenous pressure is equal to at most 100 bars.

11. The process according to claim 10 wherein said pressure is at most 50 bars.

12. The process according to claim 10 wherein said reaction is carried out in a stream of hydrogen iodide with continuous removal of the hydrogen chloride produced.

13. The process according to claim 1 wherein in the formulae A and B:
  of X' and X", one is chlorine or hydrogen, and the other is chlorine; and
  R', R" and R'" are chlorine or hydrogen, except that at most two of R', R" and R'" are hydrogen.

14. The process according to claim 13, wherein said meta-chloroaniline B is 3,5-dichloroaniline.

15. The process according to claim 13, wherein said meta-chloroaniline B is 3-chloroaniline.

* * * * *